United States Patent [19]

Moore

[11] Patent Number: 4,833,629

[45] Date of Patent: May 23, 1989

[54] APPARATUS FOR CATEGORIZING AND ACCUMULATING EVENTS

[75] Inventor: Robert C. Moore, Laurel, Md.

[73] Assignee: The Johns Hopkins University, Baltimore, Md.

[21] Appl. No.: 73,799

[22] Filed: Jul. 14, 1987

[51] Int. Cl.[4] .............................................. G06F 15/20
[52] U.S. Cl. .................................... 364/555; 364/200; 377/26
[58] Field of Search ........... 364/550, 555, 416, 571.07, 364/200; 324/71.4; 377/11, 13, 15, 16, 10, 26, 49

[56] References Cited

U.S. PATENT DOCUMENTS

| | | | |
|---|---|---|---|
| 3,906,194 | 9/1975 | Fairbairn | 377/26 |
| 4,180,724 | 12/1979 | Councilman et al. | 377/26 |
| 4,192,130 | 3/1980 | Takeuchi | 377/26 |
| 4,488,248 | 12/1984 | Okeda et al. | 364/555 |
| 4,491,926 | 1/1985 | Okeda et al. | 364/555 |
| 4,580,093 | 4/1986 | Feir et al. | 377/11 |
| 4,663,770 | 5/1987 | Murray et al. | 377/15 |

*Primary Examiner*—Parshotam S. Lall
*Assistant Examiner*—Ellis B. Ramirez

*Attorney, Agent, or Firm*—Robert E. Archibald; Francis A. Cooch

[57] ABSTRACT

Apparatus for categorizing and accumulating a plurality of different event types wherein the characteristics of each event are detected by a detector and presented to the apparatus as an electrical signal of variable analog or digital value which may indicate the type, speed, energy level or the like of an event. The apparatus includes a table look-up storage device having a plurality of individually addressable memory locations which receives the electrical or digital value and in response thereto outputs a bin address or clock select number which identifies a particular bin. Clock distribution logic circuitry receives the bin address from the look-up table storage device and in accordance with the bin address selects a particular bin and increments the event count being accumulated therein. Counter select logic circuitry is also provided for use by a host computer or the like to select a particular bin and output the event count being accumulated in the selected bin. The event count is output in a stabilized form by an output multiplexer circuit for analysis, record keeping, monitoring or the like.

20 Claims, 8 Drawing Sheets

APPARATUS FOR CATEGORIZING AND ACCUMULATING EVENTS

STATEMENT OF GOVERNMENT INTEREST

The Government has rights in this invention pursuant to Contract No. N00039-87-C-5301 awarded by the Department of the Navy.

BACKGROUND OF THE INVENTION

The present invention relates to apparatus for categorizing and accumulating events, and more particularly to an integrated circuit operable by a programmable look-up table storage device for categorizing and accumulating events.

There is a need for apparatus which can rapidly categorize and accumulate data related to microscopic particles (hereinafter referred to as particles), particularly energetic particles emanating from an energy source. Applications for such apparatus are widespread and include such diverse fields as spectrum analysis, water and air pollution studies, oil refining, bacteriology, pathology, metallurgy, basic medical research and medical diagnosis.

While some applications are accommodated by using laboratory type instrumentation, a great many other applications require instruments which can operate on-line in real time, so that the information gained from the categorizing and accumulating process is accurately recorded for later use.

Each of the various instruments used in the applications identified above has three basic elements in common: a detector, apparatus for categorizing and accumulating events, and output circuitry. The critical element in these instruments, and for which numerous devices have been proposed, is apparatus for categorizing and accumulating events.

As stated above, various devices have been proposed for categorizing and accumulating events wherein the events may be data related to particles. However, the proposed devices suffer from various disadvantages. For example, U.S. Pat. No. 4,488,248 discloses a particle-size distribution analyzer having event categorizing and accumulating apparatus which includes a particle detector adapted to produce signals in response to the size of various particles, a plurality of comparators connected in parallel to the particle detector for producing pulses related to the size of a particle, and a plurality of counters each connected to a comparator for counting the pulses produced by the comparator. Event categorization is performed by use of the comparator circuitry which must use the correct reference value in order to properly categorize the events. The accumulation of the events is performed by the counters.

Another proposed device disclosed by U.S. Pat. No. 4,491,926 provides a particle-size distribution analyzer having event categorizing and accumulating apparatus which includes a detector for generating signals proportional to the size of the detected particle, a threshold circuit adapted to remove noises or fragmental signals from the signals generated by the detector, a gate circuit adapted to decide the passage or non-passage of the detection signal through the threshold circuit, and a counter circuit adapted to count the number of detection signals generated by the gate circuit. The size of the particles is differentiated based on a threshold circuit which must be properly adjusted in order to effectively categorize the events.

As previously stated, the event categorizing and accumulating apparatus disclosed by the patents identified above suffer from various disadvantages, namely, they are slow in speed, they add numerous complicated components to what is a very simple system and they are not easily programmed or modified for use in various event categorizing and accumulating applications.

The present invention solves the above described disadvantages by providing programmable, accurate, fast and uncomplicated apparatus for categorizing and accumulating events.

SUMMARY OF THE INVENTION

According to the present invention, an apparatus for categorizing and accumulating events is provided wherein the characteristics of each event are detected by a detector and presented to the apparatus as a digital value which may indicate the type, speed, energy level, time and the like of the event. The categorizing and accumulating apparatus includes a look-up table storage device, a plurality of individually selectable bins, clock distribution logic circuitry, counter select logic circuitry and output multiplexer circuitry.

The look-up table storage device has a plurality of individually addressable memory locations wherein each memory location has stored therein a bin address which identifies a particular bin. The look-up table storage device outputs a particular bin address in response to the digital value of the event supplied to the apparatus by a detector.

Each of the individually selectable bins accumulates the count of a different event type and responds to a particular bin address.

The clock distribution logic circuitry receives the bin address from the look-up table storage device and in response thereto selects a particular bin and increments the count of the event type being accumulated therein.

The counter select logic circuitry in response to a bin address provided by a host computer or the like selects a particular bin and causes the count of the event type accumulated therein to be output in a stabilized form by the output multiplexer circuits for analysis, recording, monitoring, or the like.

BRIEF DESCRIPTION OF THE DRAWINGS

The above described features and advantages of the present invention will become apparent upon reading the following specification and by reference to the drawings in which.

DETAILED DESCRIPTION OF THE INVENTION

The present invention provides apparatus for categorizing and accumulating events, particularly energy spectra or individual particle events. The apparatus of the present invention can be used in energetic particle instruments, space telescopes, or other instruments which have a need to rapidly categorize and accumulate events. The apparatus of the present invention is designed to be implemented on an integrated circuit chip which can be easily programmed by a host computer thereby producing an extremely flexible instrument.

Figure 1:
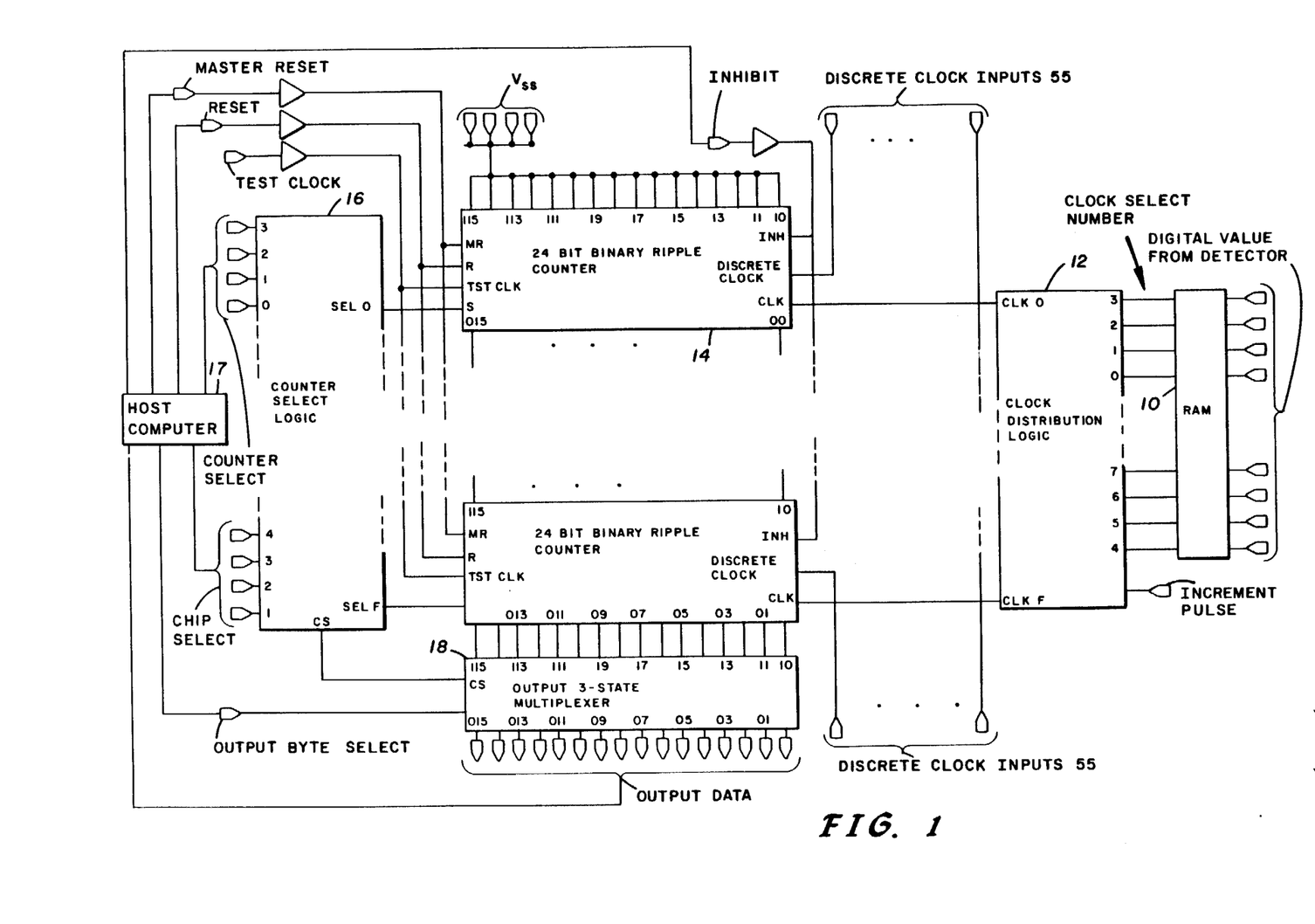
FIG. 1 is a detailed schematic diagram of a categorizing and accumulating apparatus of the present invention.

The categorizing and accumulating apparatus of the present invention as shown in FIG. 1 includes a look-up table storage device 10 having a plurality of individual addressable memory locations, wherein each memory location has stored therein a bin address or clock select number.

The characteristics of an event are detected by a detector (not shown in the drawings) and presented in the form of an electrical signal of variable analog or digital value to the look-up table storage device 10. The detector can take any form depending on the instrument and the types of events to be detected. In response to the variable analog or digital value, the look-up table storage device 10 outputs a particular bin address or clock select number. Clock distribution logic circuitry 12 receives the clock select number and in response thereto selects using a select line a particular bin 14, from a plurality of bins, and increments the count of the event type being accumulated therein.

Each bin, as shown in FIG. 1, is composed of a 24 bit binary ripple counter and is designed to consecutively count the occurrence of a single event type. The count of the event type can range from zero (0) to $2^{24}-1$. Each bin can be independently reset to zero by a reset line or all the bins may be reset to zero by a master reset line.

The apparatus of the present invention also includes counter select logic circuitry 16 which in response to a counter select number, provided by a host computer 17 or the like, selects using a select line one of the bins (24 bit binary ripple counters) and causes the count of the event type accumulated therein to be output in a stabilized form by an output multiplexer 18 for analysis, recording, monitoring, or the like.

The apparatus of the present invention, as shown in FIG. 1, can be implemented on a single integrated circuit chip wherein each chip, for example, may contain sixteen bins. A plurality of the integrated circuit chips can be operably interconnected to provide a large number of bins, for this example 256, for accumulating and categorizing a large number of different events.

In order to clarify the operation of the look up table storage device 10, as it relates to the categorizing and accumulating apparatus, a specific application of the present invention will be described. The specific application involves the use of the present invention in an energetic particle instrument or space telescope. Both devices are used for detecting, categorizing, and accumulating individual particle events. In such instruments, if both the kinetic energy of a particle and its velocity are known, then the particle mass can be determined. For particles of a given mass, kinetic energy values can be categorized and then accumulated in a plurality of bins to form an energy spectrum.

A typical particle detector used in such instruments measures both time of flight (TOF) between two fixed detector plates and the energy loss ($\Delta E$) as the particle is decelerated to zero velocity. TOF ($\Delta t$) is therefore proportional to the reciprocal of the velocity and $\Delta E$ is proportional to the mass times the square of velocity. If particles of a given mass and various energies are detected over a period of time, their loci in log $\Delta t$/log $\Delta E$ space fall on a straight line with negative slope:

$$TOF - \Delta t = K_1/v,$$

$$\text{Kinetic energy} = \Delta E = mv^2/2, \quad v^2 = 2\Delta E/m.$$

Therefore, $$\Delta t^2 = K_1^2 m/2\Delta E,$$

$$2 \log \Delta t = \log (K_1^2 m/2) - \log \Delta E, \text{ and}$$

$$\log \Delta t = K_2 - \tfrac{1}{2} \log \Delta E.$$

Figure 2:
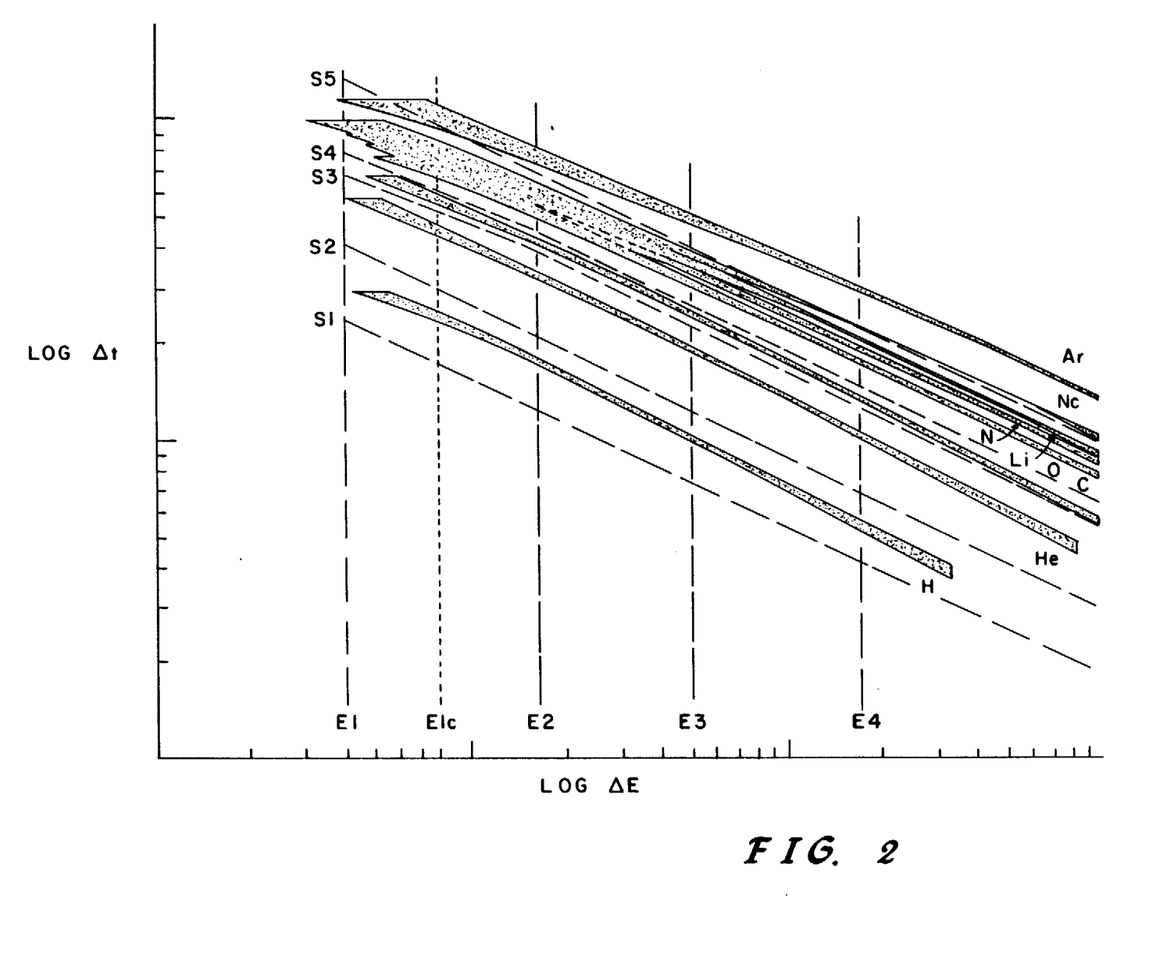
FIG. 2 is a log $\Delta t$/log $\Delta E$ graph of the distribution of various particles for measurements of time of flight versus energy lost.

FIG. 2 shows the loci (slanted regions) in log $\Delta t$/log $\Delta E$ space for ions of various masses in a typical energetic particle instrument or space telescope.

Figure 3:
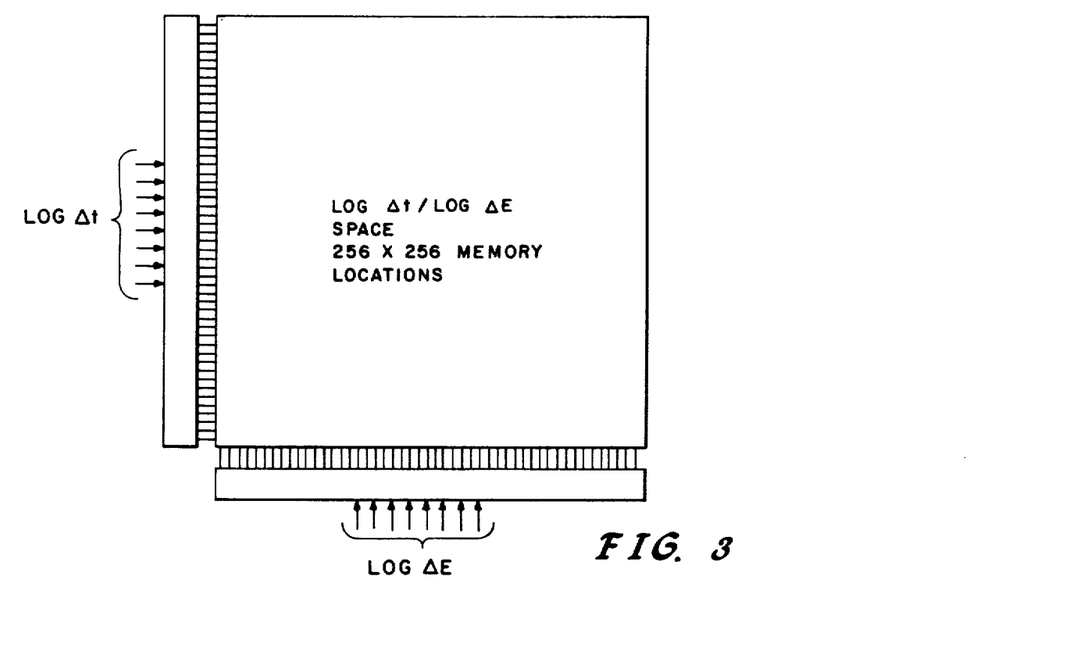
FIG. 3 is a schematic diagram of a look-up table storage device space of $256 \times 256$ memory locations square.
Figure 4:
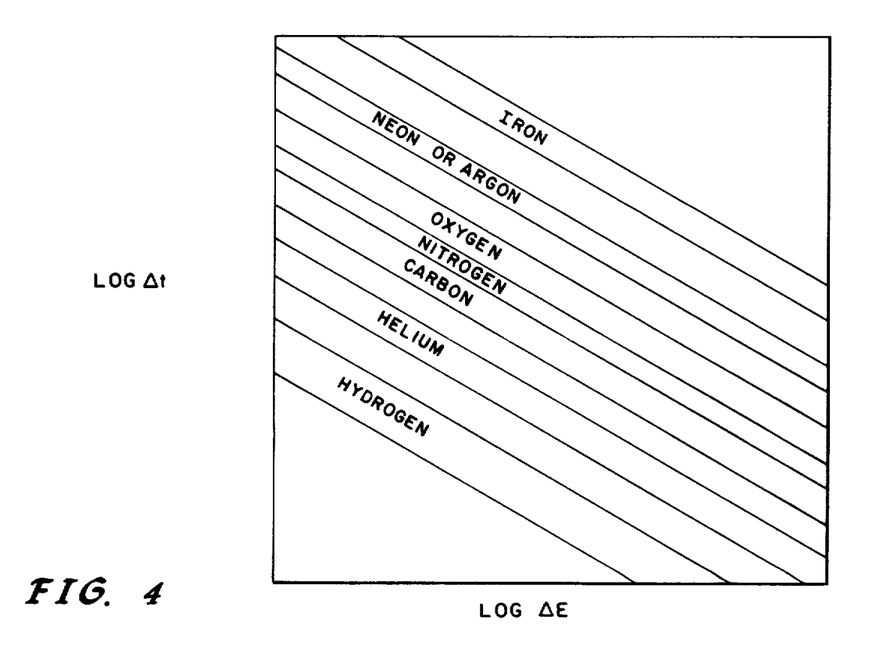
FIG. 4 is a schematic diagram of the look-up table storage device space with a plurality of slanted regions representing the distribution of different particle types.

If the instrument measures $\Delta t$ and $\Delta E$ to an accuracy of eight digital bits, then the log $\Delta t$/log $\Delta E$ space is a square array of pixels or memory locations. For this application the array, which serves as the look-up table storage device 10, is 256×256 memory locations square as shown in FIG. 3. As shown in FIG. 4, the slanted regions, having the species assignments shown in FIG. 2, can be defined in the array. The hardware required to create a square array having 256×256 memory locations is simply a 64K×8 ROM or RAM.

Figure 5:
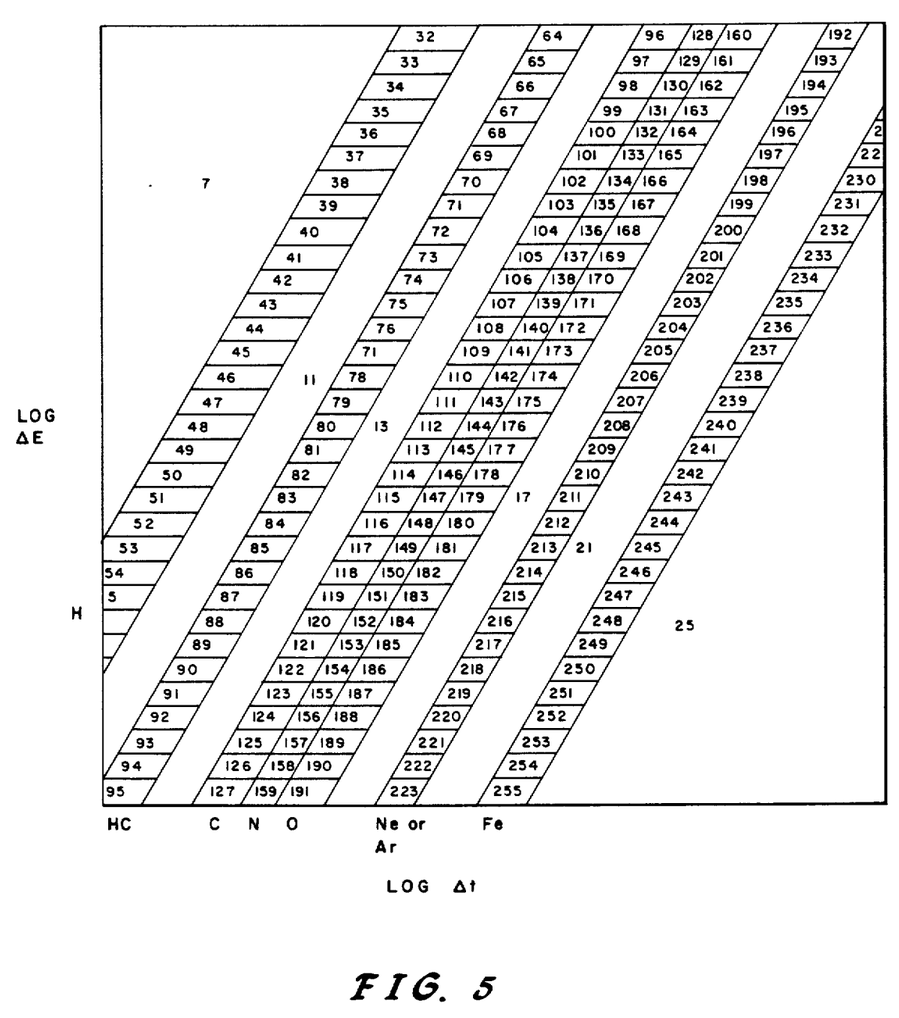
FIG. 5 is a schematic diagram of the look-up table storage device space wherein each of slanted regions includes a plurality of subregions which are assigned various bin addresses.

FIG. 5 shows each of the slanted regions divided into subregions (e.g., 32 subregions per species). Thus for each species a =bin energy spectrum can be accmulated. In addition, each of the subregions can be assigned a bin address or counter select number as shown in FIG. 5. Therefore, each subregion corresponds to a memory location and the bin address or counter select number assigned to that subregion is stored therein.

Thus, the look-up table storage device for the energetic particle instrument and space telescope application operates as follows. A particle is detected by a detector which creates a 16-bit memory address (8 bits log t, 8 bits log E). The 16 bit memory addres is applied to the look-up table storage device (the 64K×8 RAM or ROM). The look-up table storage device, in response to the 16-bit memory address, outputs an 8 bit code (bin address or counter select number) stored in the memory location being addressed. The 8 bit code identifies a particular bin having the count of the event type to be incremented. The 8 bit code is supplied to the clock distribution logic circuitry which selects using a select line the bin identified by the 8 bit code. The event count being accumulated in the selected bin is incremented by the clock distribution logic circuitry.

To further simplify the operation of the look-up table storage device, each bit of the bin address or clock select number is assigned so that different combinations of the most significant three bits of the 8 bit code uniquely identifies a different species as can be seen in Table 1 below:

| BIT 7 (MSB) | BIT 6 | BIT 5 | SPECIES | ACCUMULATORS INVOLVED |
|---|---|---|---|---|
| 1 | 1 | 1 | IRON | 224–255 |
| 1 | 1 | 0 | NEON or ARGON | 192–223 |
| 1 | 0 | 1 | OXYGEN | 160–191 |
| 1 | 0 | 0 | NITROGEN | 128–159 |
| 0 | 1 | 1 | CARBON | 96–127 |
| 0 | 1 | 0 | HELIUM | 64–95 |
| 0 | 0 | 1 | HYDROGEN | 32–63 |

Within each species the 32-bin energy spectrum is addressed by successive bin address or clock select numbers (e.g., the spectrum for hydrogen occupies accumulators numbered sequentially from 32 to 63). An array of 256 bins each of which could be addressed by a single 8-bit code, would be sufficient to accumulate the seven species spectra shown in FIGS. 2, 3, 4 and 5.

The specific example described above represents only one application of the look-up table storage device. Many other applications are possible, for example, the region of species do not have to be linear nor contiguous. The actual values of Δt and ΔE, rather than the logarithms of these values, could be used as the addresses. Also, the memory space need not be limited to two dimensions.

The advantage of using a RAM for the look-up table storage device for event categorization is that the RAM contents can be modified at will, either from a library of patterns stored in ROM or by a memory load function from a host computer. This gives the instrument investigators more science data flexibility than ever before, without introducing excessive complexity and unreliability into the apparatus.

Figures 6A, 6B:
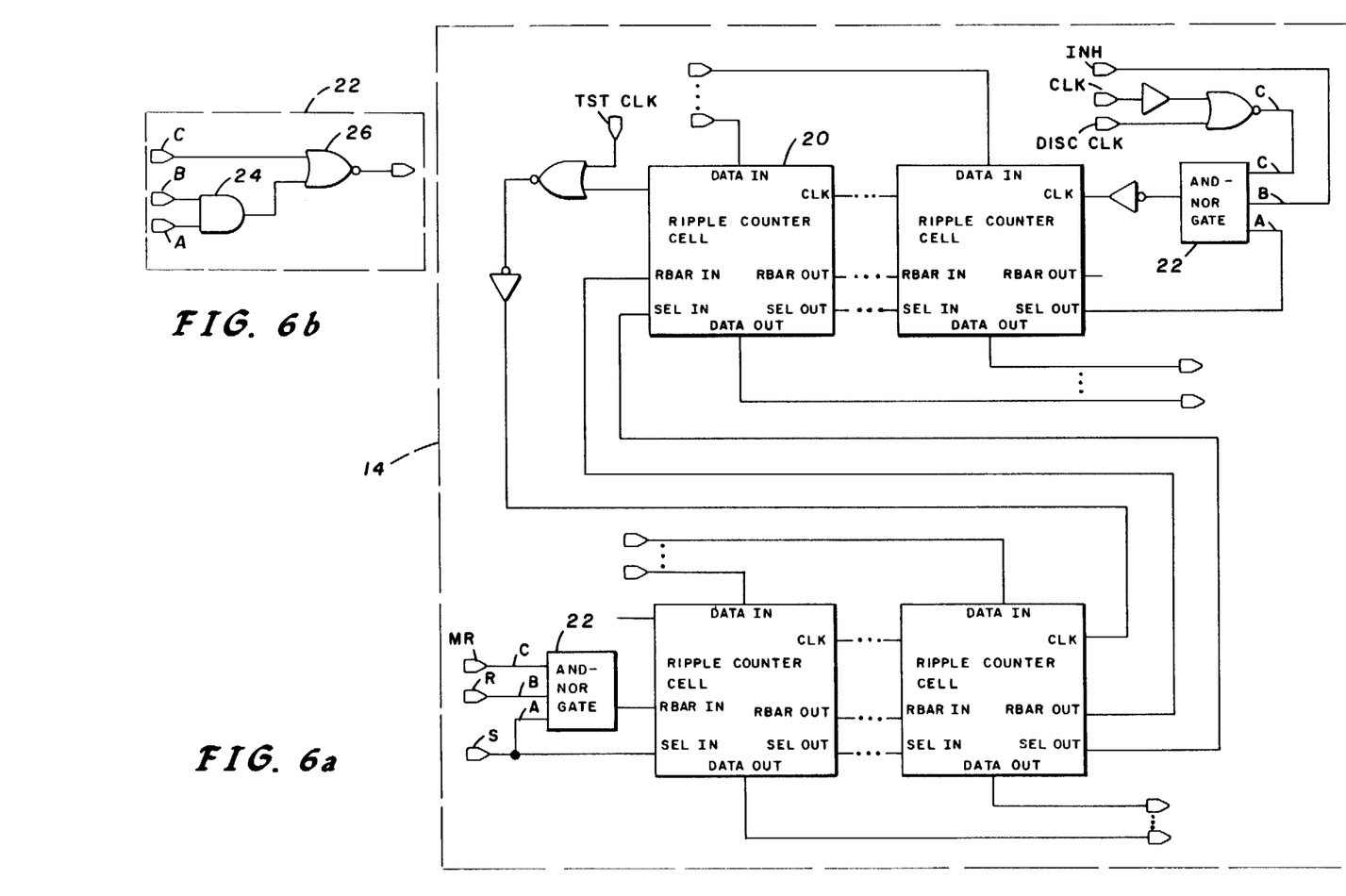
FIG. 6a is a schematic diagram of a 24-bit binary ripple counter of the present invention.
FIG. 6b is a schematic diagram of the network of an AND-NOR gate of the present invention.

FIG. 6a shows the elements of the 24-bit binary ripple counter 14. The 24-bit binary ripple counter includes a plurality of cascaded or operably interconnected ripple counter cells 20 interconnected to a plurality of AND-NOR gates 22. There are 24 ripple counter cells for each 24 bit binary ripple counter. The network for the AND-NOR gate is shown in FIG. 6b and includes AND gate 24 having its output connected to one of the inputs of a NOR gate 26.

Figure 7:
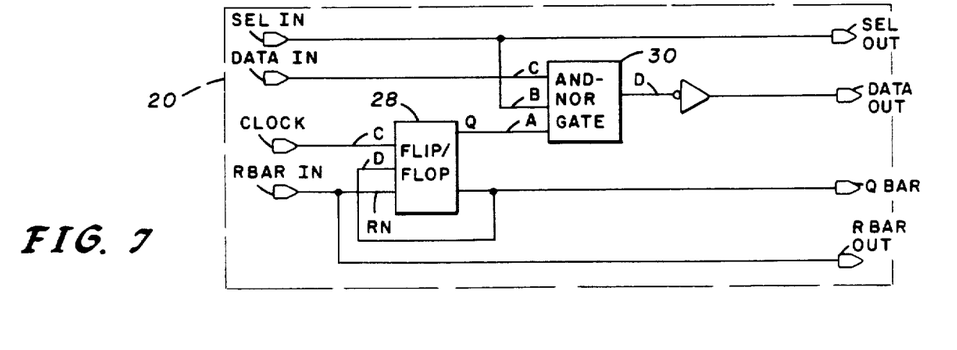
FIG. 7 is a schematic diagram of a binary ripple counter cell of the present invention.

FIG. 7 illustrates the network for the ripple counter cell 20. The ripple counter cell 20 includes a flip-flop 28 having an output connected to one of the inputs of an AND-NOR gate 30.

Figure 8:
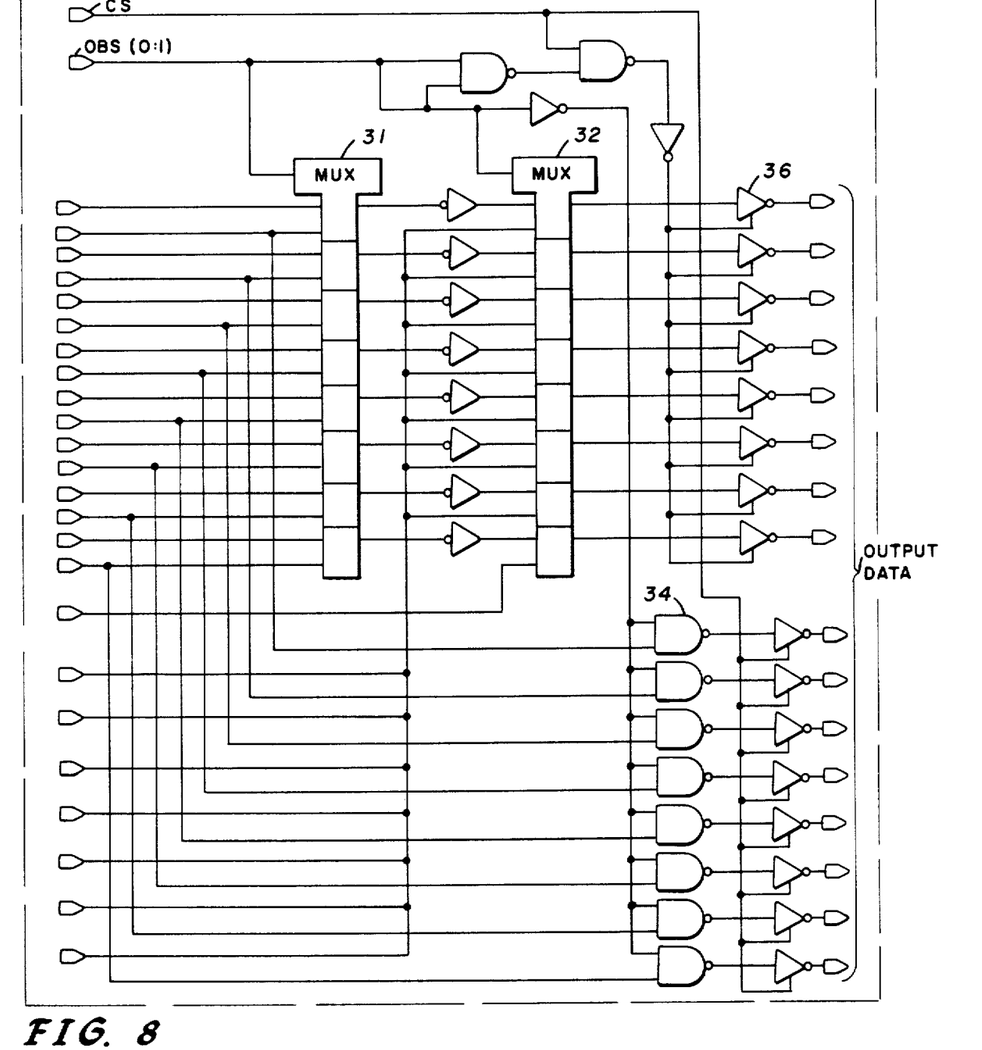
FIG. 8 is a schematic diagram of an output multiplexer of the present invention.

The output multiplexer 18, is further illustrated in FIG. 8. The output multiplexer 18 includes two byte wide multiplexers 31 and 32 interconnected to various NAND gates 34 and inverters 36 for receiving and outputting event counts from the 24-bit binary ripple counters 14.

Figure 9:
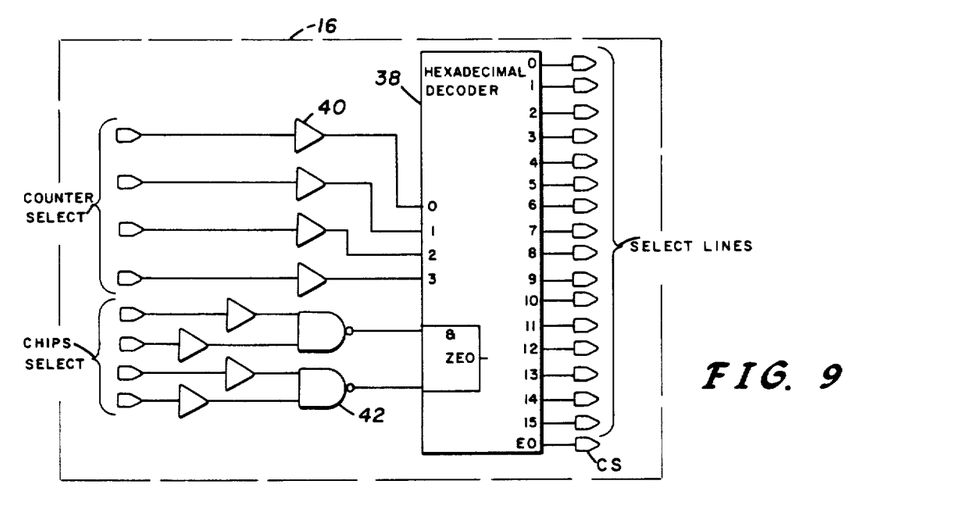
FIG. 9 is a schematic diagram of a counter select logic circuitry of the present invention.
Figure 10:
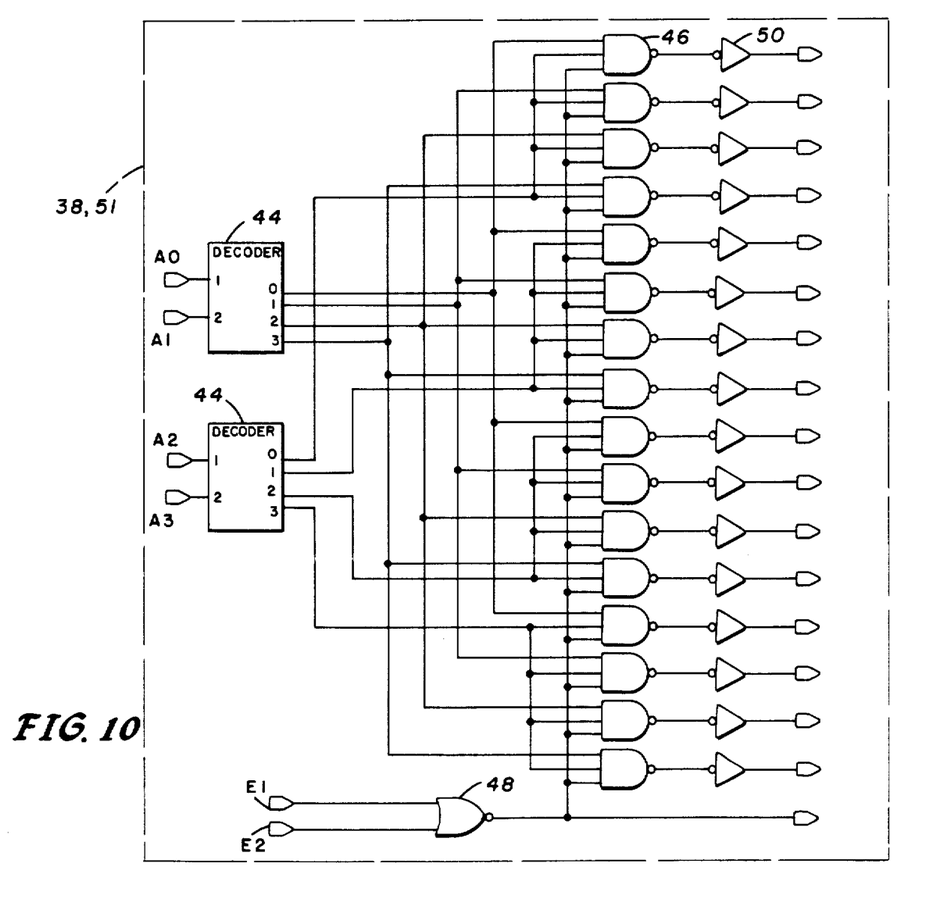
FIG. 10 is a schematic diagram of a hexadecimal decoder of the counter select logic circuitry of the present invention.

The counter select logic circuitry 16, as illustrated in FIG. 9, includes a hexadecimal decoder 38 having connected to its inputs various buffers 40 and NAND gates 42. The hexadecimal decoder 38 includes a plurality of select lines. A more detailed figure of the hexadecimal decoder is shown in FIG. 10. The hexadecimal decoder includes two 1 of 4 decoders 44 interconnected to a plurality of NAND gates 46, a NOR gate 48, and output drivers 50. The output lines of the output drivers 50 correspond to the select lines of the counter select logic circuitry as shown in FIG. 9. As described above the counter select logic circuitry 16 receives a counter select number and in response thereto selects by use of a select line a particular bin. Counter select logic circuitry causes the operation of the bin to be inhibited and the event count accumulated therein is provided to the output multiplexer 18.

Figure 11:
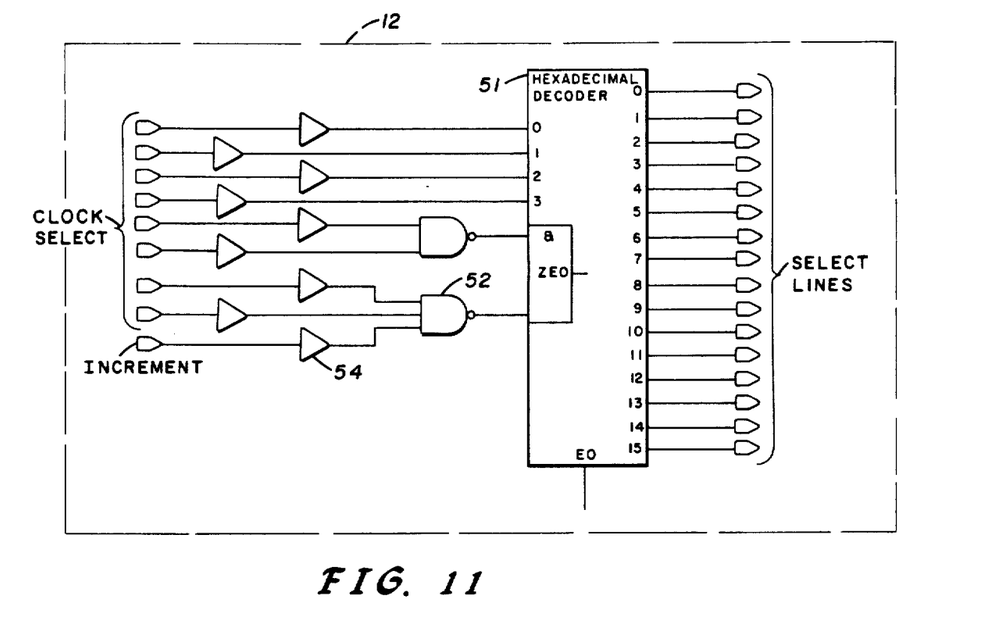
FIG. 11 is a schematic diagram of a clock distribution logic circuitry of the present invention.

FIG. 11 illustrates the clock distribution logic circuitry 12 as having a hexadecimal decoder 51 interconnected to various NAND gates 52 and buffers 54. The hexadecimal decoder 51 is shown in FIG. 10. The hexadecimal decoder 51 includes a plurality of select lines. The clock distribution logic circuitry 12 receives a bin address or clock select number and in response thereto selects by use of a select line a particular bin. An event pulse or increment pulse is steered by the clock distribution logic circuitry to the selected bin thereby incrementing the count of the event type being accumulated therein. Discrete clock inputs 55, as shown in FIG. 1, are also provided to the bins for individually incrementing the event counts by a host computer or the like.

Figure 12:
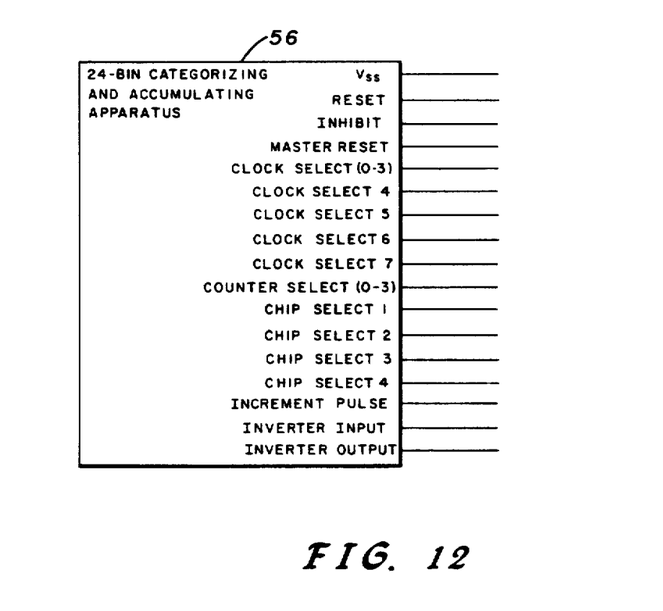
FIG. 12 is a schematic diagram representative of an integrated circuitry chip embodying the apparatus of the present invention.

Upon combining all the elements discussed above on one integrated circuit chip the categorizing and accumulating apparatus will have output and input lines, as illustrated in FIG. 12. A plurality of the categorizing and accumulating integrated circuit chips can be operably interconnected in order to provide up to 256 separate bins for categorizing and accumulating different event types.

To select and read out the contents of a particular bin, the host computer must observe the following program (see FIGS. 1 and 12 for structure): (1) the appropriate bit pattern is applied to the chip select inputs, (2) the appropriate bit pattern is applied to the counter select inputs, (3) the inhibit control signal is asserted, (4) the output byte select lines are asserted, (5) data are accepted from the output multiplexer into the host computer, (6) the reset signal is asserted briefly to clear the addressed bin to zero, (7) the inhibit signal is removed. In the host computer, this sequence of events (program) may easily be controlled using a programmable sequential array (See, Milos D. Ercegovac and Tomas Lang, *Digitial Systems and Hardware-Firmware Algorithms* (New York, NY: John Wiley and Sons, Inc., 1985) pp. 413–417) or a canonical microprogram control store (See, Milos D. Ercegovac and Tomas Lang, *Digital System and Hardware-Firmware Algorithms* (New York, NY: John Wiley and Sons, Inc., 1985) pp. 564–565). Alternatively, a general-purpose computer may easily be programmed to generate this sequence of events.

As described above, the present invention provides categorizing and accmulating apparatus for categorizing and accumulating different event types wherein the characteristics of each event are detected by a detector and presented to the apparatus as an electrical or digital value which may indicate the type, speed, energy level, time, or the like of the event.

A look-up table storage device having a plurality of individually addressable memory locations receives the digital value and in response thereto outputs a bin address or clock select number which identifies a particular bin. A clock distribution logic circuitry receives the bin address from the look-up table storage device and in accordance with the bin address selects a particular bin and increments the event count being accumulated therein. The present invention also provides counter select logic circuitry which is used by a host computer or the like to select a particular bin and output the event count being accumulated in the selected bin. The event count is output in a stabilized form by an output multiplexer circuitry for analysis, record keeping, monitoring, or the like.

Having described a preferred embodiment of a novel categorizing and accumulating apparatus in accordance with the present invention, it is believed that other modifications, variations and changes will be suggested to those skilled in the art in view of the teaching set forth herein. It is, therefore, to be understood that all such variations, modifications and changes are believed to fall within the scope of the present invention as defined by the appended claims.

What is claimed is:

1. Apparatus for categorizing and accumulating a plurality of events wherein each event is represented by an electrical signal of variable value, said apparatus comprising:
   look-up table storage means having a plurality of memory locations, each memory location having stored therein a bin address which identifies a particular bin, said look-up table storage means categorizing each of said plurality of events by outputting a bin address in response to a particular value of said electrical signal of variable value;
   a plurality of selectable bins for accumulating counts, wherein each bin accumulates a count of an event type; and
   clock distribution logic means, connecting said look-up table storage means and said plurality of selectable bins, which receives a bin address from said look-up table storage means and in response thereto selects, using a select line, a particular bin and increments the count of the event type being accumulated therein.

2. Apparatus according to claim 1 further comprising: counter select logic means which, in response to a bin address provided by a host computer or the like, selects, using a select line, a particular bin and causes the count of the event type accumulated therein to be output in a stabilized form by an output multiplexer means.

3. Apparatus according to claim 2 wherein said memory locations of said look-up table storage means are divided into a plurality of regions corresponding to different event types.

4. Apparatus according to claim 3 wherein each region, of said plurality of regions, is divided into subregions and each subregion corresponds to a memory location which has stored therein a bin address.

5. Apparatus according to claim 4 wherein each bin comprises a N-bit binary ripple counter wherein N is equal to an integer number.

6. Apparatus according to claim 5 wherein said N-bit binary ripple counter includes N ripple counter cells operably connected to one another, and each ripple counter cell corresponds to a bit of said N-bit binary ripple counter.

7. Apparatus according to claim 6 wherein each ripple counter cell comprises a flip-flop device operably connected to an AND-NOR gate.

8. Apparatus according to claim 7 wherein said output multiplexer means comprises a first multiplexer operably connected to a second multiplexer wherein said first and second multiplexers are both operably connected to a plurality of NAND gates and inverters for receiving and outputting event counts in a stabilized form.

9. Apparatus according to claim 8 wherein said clock distribution logic means comprises:
   a hexadecimal decode which is operably connected to a plurality of buffers and NAND gates, said hexadecimal decoder having select lines for selecting a bin in response to a bin address.

10. Apparatus according to claim 9 wherein said hexadecimal decoder comprises:
    first and second decoders each having four output lines, wherein each decoder receives a portion of the bin address and in response thereto actuates one of the four output lines from the decoder;
    a NOR gate which receives the remaining portion of the bin address and in response thereto actuates a select line; and
    a plurality of NAND gates, operably connected to the output lines of said first and second decoders wherein the output line of each NAND gate is operably connected to a line driver having its output line provided as a select line.

11. Apparatus according to claim 10 wherein said counter select logic means comprises:
    a hexadecimal decoder which is operably connected to a plurality of buffers and NAND gates, said hexadecimal decoder having select lines for selecting a bin in response to a bin address.

12. Apparatus according to claim 11 wherein said hexadecimal decoder comprises:
    first and second decoders each having four output lines, wherein each decoder receives a portion of the bin address and in response thereto actuates one of the four output lines from the decoder;
    a NOR gate which receives the remaining portion of the bin address and in response thereto actuates a select line; and
    a plurality of NAND gates operably connected to the output lines of said first and second decoders wherein the output line of each NAND gate is operably connected to a line driver having its output line provided as a select line.

13. A method for categorizing and accumulating a plurality of events comprising the steps of:
    receiving into a look-up table storage means having a plurality of memory locations, each memory location having stored therein a bin address which identifies a particular bin, an electrical signal of variable value which represents an event type;
    obtaining from said look-up table storage means, in response to said electrical signal of variable value, a bin address;
    selecting a particular bin from a plurality of selectable bins for accumulating counts, wherein each bin accumulates a count of an event type, in response to said bin address; and incrementing the count of the event type being accumulated in the selected bin.

14. A method according to claim 13 further comprising the steps of:
providing an output means for outputting the count of an event type whereby said output means selects a particular bin and provides the count of the event type accumulated therein to an output multiplexer means which outputs the count of the event type in a stabilized form.

15. A method according to claim 14 wherein said output multiplexer means comprises a first multiplexer operably connected to a second multiplexer wherein said first and second multiplexers are both operably connected to a plurality of NAND gates and inverters for receiving and outputting event counts in a stabilizer form.

16. A method according to claim 15 wherein said plurality of memory locations are divided into a plurality of regions corresponding to different event types.

17. A method according to claim 16 wherein each region of said plurality of regions is divided into subregions and each subregion corresponds to a memory location which has stored therein a bin address.

18. A method according to claim 17 wherein each bin comprises an N-bit binary ripple counter wherein N is equal to an even integer number.

19. A method according to claim 18 wherein said N-bit binary ripple counter includes N ripple counter cells operable connected to one another and each ripple counter cell corresponds to a bit of said N-bit binary ripple counter.

20. A method according to claim 19 wherein each ripple counter cell comprises a flip-flop device operably connected to an AND-NOR gate.

* * * * *